United States Patent [19]

Snyder

[11] Patent Number: 5,037,544
[45] Date of Patent: Aug. 6, 1991

[54] KEYED COLUMN CHROMATOGRAPHY APPARATUS

[76] Inventor: Thomas A. Snyder, c/o Berwick Corp., 447 Ivyland Rd., Warminster, Pa. 18974

[21] Appl. No.: 619,817

[22] Filed: Nov. 29, 1990

Related U.S. Application Data

[63] Continuation of Ser. No. 208,320, Jun. 17, 1988, abandoned.

[51] Int. Cl.$^5$ .............................................. B01D 15/08
[52] U.S. Cl. .................................. 210/198.2; 210/656; 55/386
[58] Field of Search ............... 210/656, 198.2; 422/70, 422/101, 99, 102; 436/161, 178; 604/197, 263; 55/386

[56] References Cited

U.S. PATENT DOCUMENTS

| D. 205,033 | 6/1966 | Barrantes | D10/1 |
|---|---|---|---|
| D. 251,644 | 4/1979 | Ravn | D6/128 |
| D. 284,700 | 7/1986 | Mehra et al. | D24/32 |
| 2,979,210 | 4/1961 | Patterson | 211/74 |
| 4,116,836 | 9/1978 | De Angelis | 55/386 |
| 4,214,993 | 7/1980 | Forsythe | 210/198.2 |
| 4,226,119 | 10/1980 | Buser | 73/864.82 |
| 4,270,921 | 6/1981 | Graas | 422/70 |
| 4,476,016 | 10/1984 | Kiyasu | 422/70 |
| 4,787,971 | 11/1988 | Donald | 422/70 |
| 4,810,471 | 3/1989 | Wachob | 422/70 |

OTHER PUBLICATIONS

The Supelco, Inc. publication form No. 97857 describes the Supelclean Disposal SPE Tubes, 1986.
The Sarstedt, Inc. publication No. 103 describes the Microvette® columns, 1985.
ANSI/HIMA MD70.1-1983, "American National Standard for Medical Material—Luer Taper Fightings—Performance" (1983).
John A. Thompson, "A Review of High Performance Liquid Chromatography in Nucleic Acids Research", BioChromatography, vol. 1, No. 1 (1986), pp. 16-20.

Primary Examiner—Ernest G. Therkorn
Attorney, Agent, or Firm—Panitch Schwarze Jacobs & Nadel

[57] ABSTRACT

Keyed column chromatography apparatus comprises a polymer body having a channel extending therethrough, means for coupling the column to insertion apparatus having complimentary coupling means, and keying means on the outer surface of the column. In addition, a collecting tube comprises a hollow body having one end having an aperture therethrough and having keying means on the outer surface of the tube. Further, a rack for receiving generally cylindrical bodies having complimentary keying means comprises a top surface and a plurality of legs sufficient to support the top surface. The kit comprising and facilitating the same method is included.

26 Claims, 2 Drawing Sheets

KEYED COLUMN CHROMATOGRAPHY APPARATUS

This application is a continuation of Ser. No. 208,320, filed June 17, 1988, now abandoned.

FIELD OF THE INVENTION

The present invention relates to apparatus for column chromatography, specifically high-performance liquid chromatography. More particularly, the present invention is directed to keyed chromatography columns, complementary keyed collecting tubes, complementary racks, and methods of using the same for column chromatography.

BACKGROUND OF THE INVENTION

Chromatography comprises a group of methods for separating a mixture of substances into their component parts. "Chromatography" is, however, a misnomer for these methods because the color of components is rarely the basis used for identifying and isolating component parts in modern techniques. Traditionally, chromatographic techniques include gas chromatography (GC) or gas-liquid chromatography (GLC), thin layer chromatography (TLC), and column chromatography, frequently called high-performance liquid chromatography (HPLC).

Column chromatography may be used to separate and identify a variety of substances, including pharmaceutical drugs, hormones, and cell constituents including deoxyribonucleic acid (DNA) and ribonucleic acid (RNA). Generally, column chromatography is a selective filtration or elution process whereby a substance or species to be chromatographed is dissolved or suspended in an eluant and passed through a porous or semi-porous bed or column of chromatographic separation material, from which an eluate may be collected.

The chromatographic separation material is typically chosen dependent upon the substances to be chromatographed. Such separation material may be generally categorized into five types: (1) size-exclusion; (2) affinity; (3) ion-exchange; (4) reversed-phase; and (5) ion pairing. See generally J. A. Thompson, "A Review of High Performance Liquid Chromatography in Nucleic Acids Research," *BioChromatography*, 1:16 (1986).

Depending upon the nature, density, and height of the column of chromatographic separation material, and the nature of the substance to be chromatographed and the eluants used, pressure may be required (or desired in the interest of time) to force the eluants and substances through the separation material. Conventional techniques include positive pressure, such as a pump or syringe, and negative pressure, such as gravity, vacuum withdrawal or centrifugation. With such a variety of techniques, versatile column chromatography apparatus is often required.

Several manufacturers have produced apparatus for use in column chromatography. For example, Supelco, Inc. manufactures Supelclean Disposal SPE Tubes, which contain silica gel-based bonded phase packings. Solutions may be passed through these tubes into collecting tubes using negative pressure by a vacuum or centrifugation, or by positive pressure by an air pump or syringe. However, the Supelco tube requires a tube adapter to be fitted for a syringe or other positive pressure source using only friction to hold the adapter and positive pressure source in communication with the tube containing the chromatographic material and eluant. Negative pressure by centrifugation is achieved by inserting the column or tube into a collecting tube and inserting this combined unit into a centrifugation device. No locking devices are present.

Sarstedt, Inc. manufactures Microvette ® columns which may be inserted into a collecting tube adapted to receive the Microvette ® columns using friction to hold the columns in place. The Microvette ® column is, however, capable of being twisted even after being inserted into the collecting tube and thus provides no secure means for coupling or uncoupling the Microvette ® columns to insertion apparatus.

Gelman Sciences Inc. manufactures filtration products for high-pressure liquid chromatography adapted to receive substances suspended in an eluant from an insertion device, such as a syringe. The Gelman devices use filters which also function as a coupling between the collecting tube and the insertion source, typically a syringe. The coupling is achieve by friction, but may be locked in place by means of an additional, external clamping device.

CooperBiomedical, Inc. manufactures a mini-spin column comprising a separation material-filled column and a collecting tube adapted to receive and hold in place the column by friction means. The column is not, however, adapted for coupling to an insertion means, such as a syringe. Further, nothing prohibits the column once inserted into the receiving collecting tube from rotating. The column contains one fibrous filter packed into the lower, tapered end of the column on top of which the bed of separation material is packed.

Apparatus made by companies including those listed above are used to chromatograph a variety of substances, including highly toxic or virulent substances. Conventional apparatus generally require that the operator or technician employing the chromatography apparatus come in contact with the apparatus during use. For example, to remove a chromatography column from a collecting tube normally requires one to pull the tube out by hand or by using clamp-like instruments. Similarly, to place a conventional chromatography column coupled to a syringe, for example, into a collecting tube, uncouple the syringe and leave the column in the tube, one must normally hold the chromatography columnmn in place to prevent the column from twisting or pulling out while the syringe is removed. Such contact places the operator or technician at risk of touching possibly toxic or virulent chemicals, drugs and genetic material. Recent research into the acquired immune deficiency syndrome (AIDS) virus is one example of genetic material which presents a deadly threat to chromatography technicians. Nothing in the prior art discloses or suggests apparatus which may be used in column chromatography while minimizing risk of exposure to the substances contained therein.

In view of the serious deficiencies and inefficiencies of the prior art, it would be desirable to have an apparatus which minimizes risk of exposure to substances contained therein, which is easy to use, and which is relatively simple and inexpensive to produce.

SUMMARY OF THE INVENTION

Briefly stated, the present invention comprises a chromatography column comprising a polymer body having a channel extending therethrough, means for coupling the column to insertion apparatus having complementary coupling means, and keying means on the outer surface of the column. The present invention further comprises a collecting tube having one end having an aperture therethrough being adapted to receive complementary keying means and having keying means on the outer surface of the tube. The present invention further comprises a rack for receiving generally cylindrical bodies having complementary keying means. Further, the present invention comprises a kit for column chromatography comprising a chromatography column, a collecting tube and a rack for receiving the chromatography column and the collecting tube, all as described above.

In addition, the present invention comprises a method of filtering fluids, which comprises drawing a fluid into an insertion apparatus having coupling means and coupling the insertion apparatus to the chromatography column described above, inserting the fluid into the inlet end of the chromatography column, inserting the chromatography column into a collecting tube having one end with an aperture therethrough adapted to receive the complementary keying means of the chromatography column, and applying pressure to the species and eluant.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there is shown in the drawings an embodiment that is presently preferred, it being understood, however, that the invention is not limited to the specific arrangements and instrumentalities disclosed. In the drawings.

DETAILED DESCRIPTION OF PREFERRED EMBODIMENTS

Figure 1:
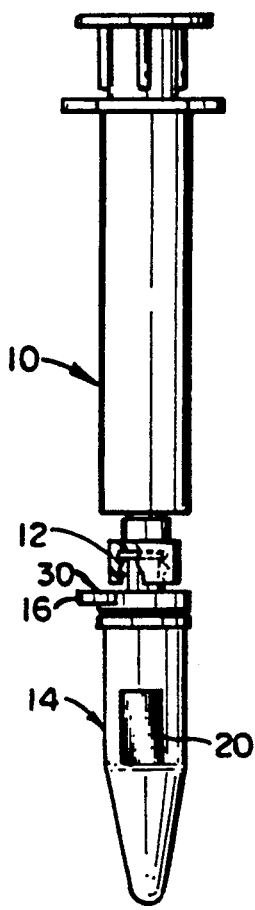
FIG. 1 is a front elevational view of a keyed chromatography column in accordance with the present invention shown inserted into a collecting tube in accordance with the present invention and attached to an insertion device (here a medical syringe) and FIG. 1 also contains a partial cross-sectional view showing coupling means on the chromatography column in accordance with the present invention and complementary coupling means on the insertion device.

Referring to the drawings, wherein like numerals indicate like elements throughout, there is shown in FIGS. 1 through 6 keyed column chromatography apparatus in accordance with the present invention.

According to the present invention, keyed column chromatography apparatus comprises a chromatography column 30 comprising a polymer body, which has an open top end face 31 and an open bottom end face 33 and a channel 37 extending therethrough from the top end face 31 to the bottom end face 33, where the channel 37 is generally circular and tapered from the top end face 31 to the bottom end face 33, the diameter of the channel 37 at the bottom end face 33 being smaller than the diameter of the channel 37 at the top end face 31.

The outer surface of the chromatography column 30 generally defines four segments. The first segment 44 has a generally circular shape in cross-section and is generally uniform in cross-section along the length thereof. The second segment 46 is generally circular in cross-section and is tapered from one end of the second segment 46 to the other end of the second segment 46. The third segment 48 is generally circular in shape in cross-section and has a generally uniform shape in cross-section along the length thereof. The diameter of the outer surface of the third segment 48 is generally smaller than the diameter of the outer surface of the first segment 44. Finally, the fourth segment 49 of the chromatography column 30 according to the present invention has a generally circular shape in cross-section and is substantially tapered from one end of the fourth segment 49 to the other end of the fourth segment 49.

Preferably, the polymer body comprises polypropylene, polyethylene, polyethylene terephalthane glycol (PETG), nylon, polycarbonate, Barex, polyester, polypropinate, polytetrafluoroethylene (Teflon), polyvinyl chloride, polysulfone and polystyrene. More preferably, the polymer body comprises polypropylene. Generally, the polymer should be resistant to chemical action and thermal degradation and, preferably, should be fairly resistant to pressure exerted on the polymer body, specifically pressure from within the channel 37 of the polymer body. One skilled in the art will recognize that other, similar polymers, preferably exhibiting these properties, may be used in accordance with the present invention.

The polymer body of the chromatography column 30 may be formed using methods and techniques known in the art for molding polymer bodies. For example, in one embodiment of the present invention, the polymer body is formed by injection molding. One skilled in the art will appreciate, however, that other methods and techniques for forming polymer bodies may be used in accordance with the present invention.

The channel 37 of the chromatography column 30 is adapted to receive at least one porous filter 36 which is securely positioned within the channel 37. Generally, the filter 36 is circular or disk-shaped to conform to the cross-sectional shape of the channel 37 through the column 30 and preferably comprises plastic selected from the group consisting of polyvinylidene difluoride, cellulose, polysulfone, polypropylene, nylon and polytetrafluoroethylene. More preferably, the porous filter 36 comprises porous plastic. Examples of such filters 36 include FP Vericel, GN Metricel, HT Tuffryn, Metricel, polypropylene, Nylaflo, Versapor and glass fiber filters, all known in the art and described generally in "Separation Products for Molecular Biology", *The Filter Book,* at 153-55 (Gelman Science: 1988).

The type and density or porosity of the porous filter 36 depends on the type and viscosity of the fluid to be filtered (discussed below) and the desired filtration to be performed. One skilled in the art may readily determine the type and porosity of the porous filter 36, based on the filtration or chromatograph to be performed using the chromatography column 30 in accordance with the present invention.

The porous filter 36 may be securely positioned within the channel 37 of the chromatography column 30 by positioning the filter 36 in engagement with a retaining ring 38 inwardly protruding into the channel 37 of the chromatography column 30. Such a retaining ring 38 may be, for example, an integral part of the polymer body, formed during the molding of the polymer body as described above. Where desired, a pair of retaining rings 38 may be positioned in the channel 37 so that the filter 36 is intermediate and in engagement with the pair of retaining rings 38.

The filter 36 may also be securely positioned by placing a filter 36 having a predetermined diameter into the tapered channel until the filter 36 becomes wedged ar a point where the diameter of the channel 37 is smaller than the diameter of the filter 36 and can move no further, and positioning a retaining ring 38 in engagement with the side of the filter 36 toward the channel 37 having a larger diameter (i.e., distal the smaller diameter channel 37 proximal to the bottom end face 33).

In another example of the present invention, retaining rings 38 may be heat welded into the channel 37 of the chromatography column 30. In another example, a porous filter disk 36 may have a diameter larger than the diameter of the channel 37 in the chromatography column 30 and a circular groove may be cut into the channel 37 to securely receive such a porous filter disk 36. One skilled in the art will recognize that other similar methods and techniques may be used to securely position a porous filter 36 within the channel 37 of the chromatography column 30 in accordance with the present invention.

The channel 37 of the chromatography column 30 is further adapted to receive a bed of chromatographic separation material 40 positioned within the channel 37 adjacent the porous filter 36. Preferably, the separation material 40 comprises silica, cellulose, dextran, agarose, sepharose, sephadex, hydroxyapatite and paired-ion chromatography system resin. More preferably, the separation material 40 comprises paired-ion chromatography system resin. One skilled in the art will appreciate, however, that other separation materials may be used in accordance with the present invention.

In one embodiment of the present invention, the column 30 has a porous filter 36 and a bed of separation material 40 in the channel 37. The separation material 40 is generally held in place by the porous filter 36, which is preferably placed proximal to the bottom end face 33 of the chromatography column 30 and securely positioned thereat.

In another embodiment of the present invention, the column 30 has a pair of porous filters 36, which are securely positioned in the channel 37, and a bed of separation material 40 positioned intermediate the pair of filters 36 in the channel 37 of the column 30. Where the separation material 40 is positioned between two securely fastened filters 36, the material 40 will be held in place more securely and uniformly, resistant to any positive and/or negative forces exerted on the separation material 40 and any fluids passed therethrough. Preferably, the separation material 40 and at least one porous filter 36 is substantially present in the channel through the third segment 48. The amount and type of separation material is purely dependent upon the desired chromatographic separation to be performed and may be readily determined by one skilled in the art.

Figure 6:
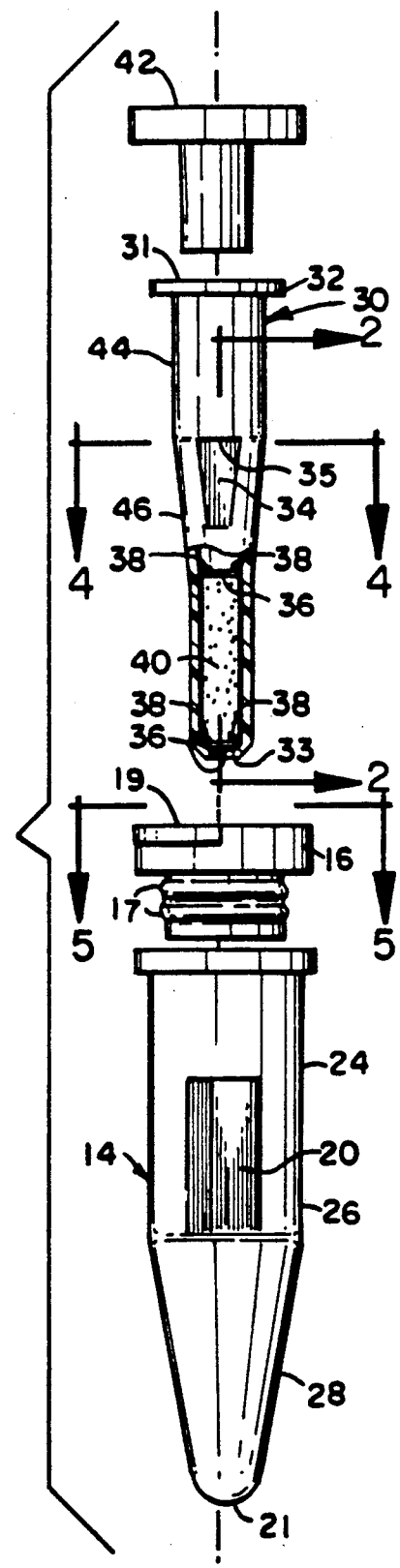
FIG. 6 is an exploded diagram showing a front elevational view of a cap which may be inserted into the chromatography column, which is shown as a partial cross-sectional view of a front elevational view of the chromatography column, which, in turn, may be inserted into the collecting tube, which is shown as a front elevational view of the collecting tube having a removable top end in accordance with the present invention.

Further in accordance with the present invention, the column 30 has means positioned at the top end face 31 of the column 30 for coupling the column 30 to insertion apparatus, such as the syringe 10 illustrated in FIGS. 1 and 6, which has complementary or reciprocal coupling means. It will be understood, however, that other insertion apparatus having complemental coupling means may be used in accordance with the present invention.

It is preferred, in accordance with the present invention, that means for coupling the column 30 to insertion apparatus comprises at least one lug 32 protruding from the periphery of the top end face 31 of the column 30. More preferably, means for coupling the column 30 to insertion apparatus comprises two lugs 32 opposingly protruding from the periphery of the top end face 31 of the column 30. More preferably still, means for coupling the column 30 to insertion apparatus comprises a female luer lock.

Luer locks are known in the art as effective coupling means. The American National Standard Institute (ANSI) describes such luer locks for use in, for example, connecting two medical devices, such as a syringe and a needle, as a liquid leak-proof and mechanically secure method which permits the two devices to be readily separated. Typically, a luer lock comprises two mating tapered fittings, commonly called a luer slip, that are slip-fitted into each other with sufficient force to effect a leak-proof connection.

In one embodiment of the present invention, the channel 37 through the chromatography column 30 is formed so that the channel 37 proximal to the top end race 31 of the column 30 forms a female luer taper. A pair of lugs opposingly protruding from the periphery of the top end face 31, in combination with the female luer taper formed in the channel 37 of the chromatography column 30, forms a female luer lock fitting ANSI standards. One skilled in the art will appreciate, however, that other coupling means may be used in accordance with the present invention.

Figure 3:
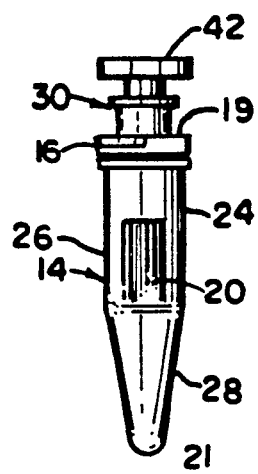
FIG. 3 is a front elevational view of a keyed chromatography column having a cap inserted thereinto showing the chromatography column as inserted into a collecting tube in accordance with the present invention.
Figure 4:
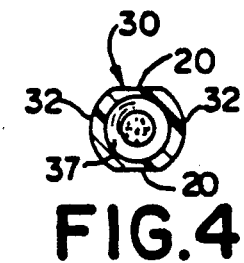
FIG. 4 is a cross-sectional view of the keyed chromatography column along line 4—4 in FIG. 6.
Figure 2:
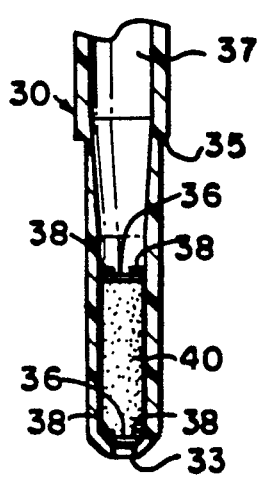
FIG. 2 is a cross-sectional view of the keyed chromatography column along line 2—2 in FIG. 6.

Complemental coupling means on an insertion apparatus, such as a syringe 10 preferably comprises a male luer lock 12 as illustrated in the partial sectional view of FIG. 1. One skilled in the art will recognize, however, that other complemental coupling devices, such as a male luer taper, may be used as complemental coupling means in accordance with the present invention. One example of device having a male luer taper is illustrated in FIGS. 3 and 6 showing a cap 42 comprising a male luer taper which may be firmly inserted into the channel 37 having a complemental female luer taper, thereby securely engaging the walls of the channel 37 and sealing the channel 37 proximal to the top end face 31.

It has been found that difficulty and risk of exposure to fluids arises when interlocking or coupling to and unlocking or uncoupling chromatography columns 30 from insertion apparatus, such as syringes, pumps and resevoirs, among others. To firmly engage or disengage a female luer lock on a chromatography column 30 to a male luer lock 12 on syringe 10, for example, it is generally required to exert a torquing force, typically by grasping the chromatography column 30 by hand or with gripping tools. In accordance with the present invention, the chromatography column 30 has at least one keying means on the outer surface of the column 30, which interrupts the generally circular shape of the outer surface thereof, and is positioned between the two end faces (31 and 33) of the column 30. It will be understood with regard to the present invention, that "keying means" are means which prevent the column 30 from being twisted about its longitudinal axis when a torquing force is applied along such axis and when the column 30 is inserted or keyed into apparatus adapted to receive said keying means.

In one embodiment of the present invention, the keying means comprises a generally flat, planar surface 34 formed on the outer surface of the second segment 46 of the chromatography column 30. In another embodiment of the present invention, the keying means comprises two opposing generally flat, planar surfaces 34 formed on the outer surface of the second segment 46 of the column 30. One skilled in the art will appreciate, however, that other keying means may be used in accordance with the present invention.

For example, a chromatography column 30 may be formed having protruding ridges longitudinally extending along the outer surface thereof; generally flat, planar surfaces 34, such as those described above, may be formed on the outer surface of the first segment 44 or the third segment 38; longitudinally extending grooves may be formed on the outer surface of the column 30; a chromatography column 30 may have lugs protruding outwardly from the outer surface thereof. One skilled in the art will also appreciate, however, that a generally flat, planar surface 34 formed on the outer surface of the column 30 is effective and relatively easy to manufacture.

Preferably, keying means comprising a planar surface 34 is adapted to form a stop 35 at the end of said keying means proximal to the top end face 31 of the column 30. One skilled in the art will recognize that such stop 35 may be used to halt the insertion of the column 30 into an apparatus adapted to receive the column 30 having keying means, at a predetermined interval, i.e., the point at which the stop 35 is located on the outer surface of the column 30.

Figure 5:
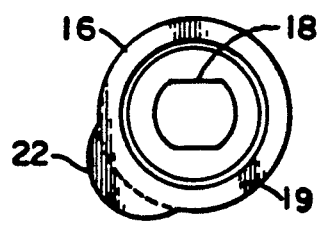
FIG. 5 is a top plan view of the collecting tube along line 5—5 in FIG. 6.

FIGS. 3, 5 and 6 illustrate a collecting tube 14 in accordance with the present invention. A collecting tube 14 comprises a hollow body having a closed bottom end face 21 and a top end face 19 having an aperture 18 therethrough. Generally, the hollow body of the collecting tube 14 has a circular hollow therein having a diameter large enough to receive, for example, the chromatography column 30 therein. The aperture 18 is adapted to receive complemental keying means, in particular, the keying means present on the outer surface of the chromatography column 30 described above.

The outer surface of the collecting tube 14 defines a first tube segment 24 having a generally circular shape in cross-section which is generally uniform in cross-section along the length thereof. In addition, the outer surface of the collecting tube 14 defines a second tube segment 26 having a generally circular shape in cross-section, which may be generally uniform in cross-section along the length thereof or tapered from the end of the second tube segment 26 proximal to the top end face 19 to the end of the second tube segment 26 distal to the top end face 19. The outer surface of the collecting tube 14 also defines a third tube segment 28 having a generally circular shape in cross-section and tapered from the end of the third tube segment 28 proximal to the top end face 19 to the end of the third tube segment 28 distal to the top end face 19.

Further in accordance with the present invention, the collecting tube 14 has at least one keying means on the outer surface of the tube 14, which interrupts the generally circular shape thereof which is positioned between the two end faces (19 and 21) of the collecting tube 14. In one embodiment of the present invention, the keying means on the outer surface of the collecting tube 14 comprises at least one flat, planar surface 20 formed on the outer surface of the second tube segment 26 of the tube 14. One skilled in the art will understand that the keying means on the outer surface of the collecting tube 14 may be provided in the same manner as the keying means positioned on the outer surface of the chromatography column 30 described above. It will be further understood that similar parameters, methods and materials may be employed to position keying means on the outer surface of the collecting tube 14 as were employed to position keying means on the outer surface of the chromatography column 30 described above.

It is presently preferred that the body of the collecting tube 14 comprises polymer or glass. More preferably, the body comprises polymer. Examples of polymers which may be used to form the body of the collecting tube 14 in accordance with the present invention include polyvinylidene difluoride, cellulose, polysulfone, polypropylene, nylon and polytetrafluoroethylene. It is particularly preferred that the body of the collecting tube comprises polypropylene. One skilled in the art will recognize, however, that other, similar polymers may be used in accordance with the present invention.

Further, it will be understood that the body of the collecting tube 14 may be comprised of other suitable materials, such as metal. Suitable materials preferably include those materials capable of resisting chemical action and withstanding relatively high forces typically downwardly directed within the hollow body occurring, for example, where a collecting tube 14 containing fluid is used in centrifugation apparatus. One skilled in the art may readily determine the material desired to be used to form the body of the collecting tube 14 in accordance with the present invention.

The aperture 18 through the top end face 19 of the collecting tube 14 preferably has a generally circular shape, interrupted by at least one flat, planar surface, which corresponds and is adapted to receive complemental generally cylindrical configurations having keying means as described above. In particular, the aperture 18 is preferably adapted to receive the complementary keying means present on the outer surface of the chromatography column 30 described above. For example, where two opposing keying means comprising generally flat, planar surfaces 34 are formed on the outer surface of the chromatography column 30, the aperture 18 through the top end face of the collecting tube 14 preferably has a generally circular shape interrupted by two opposing flat, planar surfaces corresponding in relative shape and relative position to the complemental flat, planar surfaces 34 formed on the outer surface of the chromatography column 30.

It is presently preferred that the configuration of the aperture 18 through the top end face 19 of the collecting tube 14 corresponds to the complemental configuration of a cross-section through the chromatography column 30 at a point where the keying means is positioned (as, for example, along line 4—4 in FIG. 6). One skilled in the art may readily determine the desired configurations of the aperture 18 through the top end face 19 of the collecting tube 14 in accordance with the present invention.

It may be desired that the top end face 19 of the collecting tube 14 having an aperture 18 therethrough is adapted to be removable. One skilled in the art will recognize that a removable top end face 19 may facilitate recovery of any fluid present in the collecting tube 14 during or after use of the collecting tube 14 with, for example, a chromatography column 30, especially where the aperture 18 has a diameter substantially smaller than the inner diameter of the hollow body of the collecting tube 14. In one embodiment of the present invention, a removable top end face 19 comprises a collecting tube cap 16 as illustrated in FIGS. 3, 5 and 6.

The collecting tube cap 16 preferably comprises a polymer selected from the group described above for the body of the collecting tube 14 and may be the same as or different than the material used to form the collecting tube 14. It is preferred that the cap 16 is adapted to securely fasten to the body of the collecting tube 14. For example, a top end face comprising a collecting tube cap 16 having an aperture 18 therethrough as described above, comprises a male fitting which inserts into the hollow body of the collecting tube 14 and further comprises pressure ribs 17 outwardly protruding from the portion of the cap 16 that inserts into the collecting tube 14, as illustrated in FIG. 6. It may be further desired to form a lip 22 outwardly protruding from the cap 16 to facilitate removal of the cap 16 from the collecting tube 14. Such collecting tube caps 16 are, without an aperture 18 therethrough as described above, known in the art and available from manufacturers including Sarstedt, Inc. One skilled in the art will appreciate, however, that other removable top end faces 19 may be used in accordance with the present invention.

Figure 7:
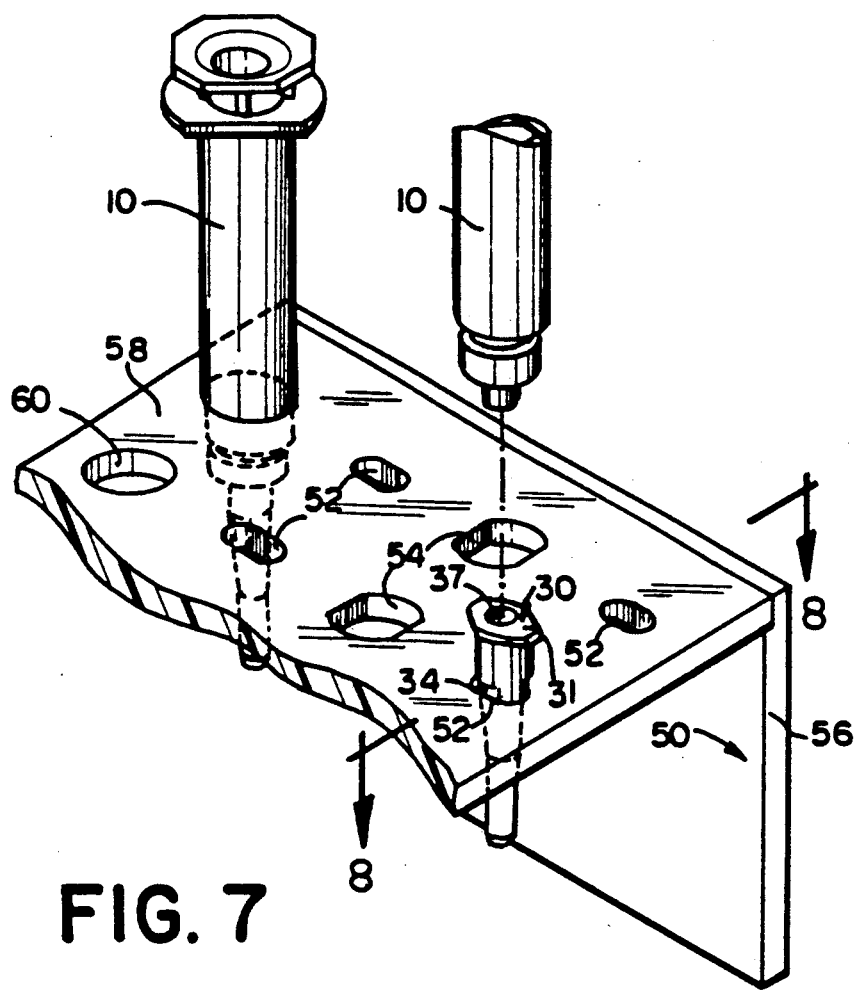
FIG. 7 is an isometric view showing a stand and illustrating keyed apertures adapted to receive the keyed chromatography column and collecting tube shown in FIG. 6.
Figure 8:
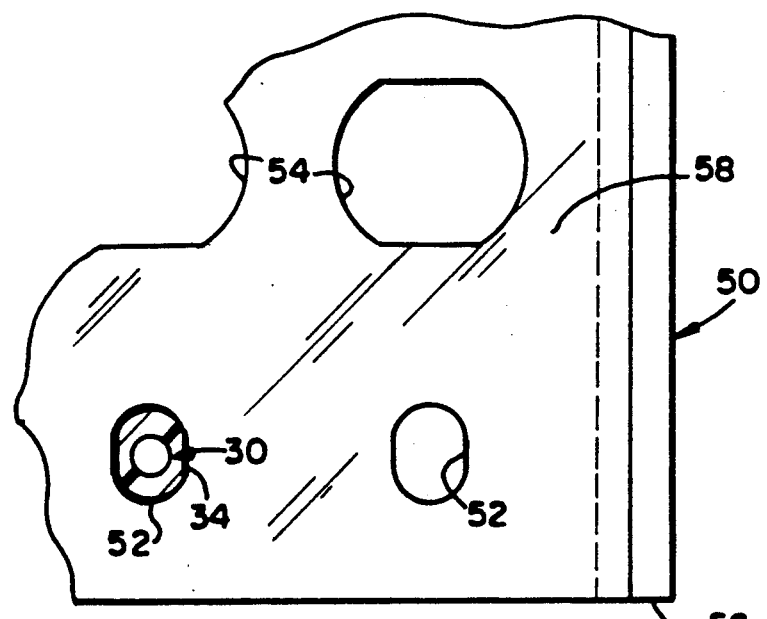
FIG. 8 is a top plan view of a keyed stand having therein a keyed chromatography column according to the present invention.

The present invention further provides a rack 50 for receiving generally cylindrical bodies having keying means on the outer surfaces thereof. FIGS. 7 and 8 illustrate a rack 50 comprising a top surface 58 having a plurality of apertures therethrough, said apertures being adapted to receive keying means, and a plurality of legs 56 sufficient to support the surface of the rack. Preferably, some of the apertures 52 through the surface 58 of the rack 50 are adapted to receive the keying means of the chromatography column 30 described above. In addition, it is preferred that some apertures 54 through the surface 58 of the rack 50 are adapted to receive the keying means of the collecting tube 14 described above. Further, it may be desired to have apertures 60 through the surface 58 of the rack 50 which are not adapted to receive keying means but are merely adapted to receive generally cylindrical bodies. One skilled in the art may readily determine the number and location of apertures, some of which may be designed to receive keying means.

It may also be desired to have a rack 50 having means for positioning the rack 50 over complementary positioned collecting means (not shown). One example of collecting means is a tray for collecting fluid. For example, the rack 50 may have positioning means comprising a plurality of lugs (not shown) downwardly protruding from the legs of the rack s  that the lugs may be received by complementary apertures through the collecting means. It will be understood that other, similar positioning means may be used on a rack 50 in accordance with the present invention.

The apparatus of the present invention (viz.: chromatography column 30; collecting tube 14; rack 50) maybe used individually or in combination to filter fluids. According to the present invention, a fluid may be filtered by drawing the fluid to be filtered into an insertion apparatus having coupling means, such as a syringe 10 having a male luer lock 12, and coupling the insertion apparatus to the chromatography column 30 described above. The chromatography column 30 preferably has at least one porous filter 36 securely positioned within the channel 37 of the column 30. More preferably, the chromatography column 30 has a pair of porous filters 36 securely positioned in a spaced relation to one another within the channel 37 of the column 30 and a bed of chromatographic separation material 40 intermediate the pair of porous filters 36 within the channel 37 of the column 30. After coupling the insertion apparatus to the chromatography column 30 to create a sealed communication therebetween, the fluid is inserted into the top end face 31 of the chromatography column 30.

The chromatography column 30 is inserted into the collecting tube 14 described above and pressure is applied to the fluid to force the fluid through the chromatography column 30. The pressure may be applied using, for example, the insertion apparatus or, preferably, the insertion apparatus may be removed, said removal being facilitated by the keying means of the column 30 being received through the aperture 18 of the collecting tube 14, placing the collecting tube 14 having the chromatography column 30 inserted therethrough into a centrifugation device, for example, and applying, through centrifugal force, negative pressure to the fluid. One skilled in the art will appreciate that the method of the present invention may be readily adapted to many chromatographic methods and techniques known in the art.

The practice of the method of the present invention may be facilitated by a kit including a chromatography column 30, a cap 42, a collecting tube 14 and a rack 50, all as described above. Such a kit may be individually designed to include some or all of the above as may be desired for a particular use. One skilled in the art may determine the desired composition of a kit including the apparatus and methods of the present invention.

The present invention may be embodied in other specific forms without departing from the spirit or essential attributes thereof and, accordingly, reference should be made to the appended claims, rather than the specification, as indicating the scope of the invention.

I claim:

1. A chromatography column comprising:
   (a) a body having an open top end face and an open bottom end face, and a channel having at least one porous filter positioned within the channel and having a bed of chromatographic separation material positioned within the channel adjacent the porous filter, said channel extending through the body from the top end face to the bottom end face, the diameter of the channel at the bottom end face being smaller than the diameter of the channel at the top end face, said channel being generally circular and tapered from the top end face to the bottom end;

(b) means positioned at the top end face of the column for securely coupling of the column to insertion apparatus having reciprocal coupling means; and (c) at least one keying means on the outer surface of the column, which interrupts the generally circular shape of the outer surface thereof, positioned between the two end faces of the column for preventing rotation of the column when the keying means engages a complementary surfaces.

2. The column according to claim 1, wherein the outer surface of the column defines a first segment having a generally circular shape in cross section and generally uniform in cross section along the length thereof, a second segment having a generally circular shape in cross section and tapered from one end of the second segment to the other end of the second segment, a third segment having a generally uniform shape in cross section and a generally uniform shape in cross section along the length thereof, the diameter of the outer surface of the third segment being smaller than the diameter of the outer surface of the first segment and a fourth segment having a generally circular shape in cross section and substantially tapered from one end of the fourth segment to the other end of the fourth segment.

3. The column according to claim 2, wherein the keying means comprises a generally flat, planar surface formed on the outer surface of the second segment of the column.

4. The column according to claim 3, wherein one end of said planer surface is adapted to form a stop adjacent to the surface of the first segment.

5. The column according to claim 2, which comprises two opposing keying means, each of said keying means comprising a generally flat, planar surface formed on the outer surface of the second segment.

6. The column according to claim 2, wherein at least one porous filter and the bed of chromatographic separation material is substantially present in the channel through the third segment.

7. The column according to claim 1, wherein the body comprises a polymer.

8. The column according to claim 7, wherein the polymer is selected from the group consisting of polypropylene, polyethylene, polyethylene glycol and polystyrene.

9. The column according to claim 1, wherein the coupling means comprises at least one lug protuding from the periphery of the top end face.

10. The column according to claim 1, wherein the coupling means comprises a female luer lock.

11. The column according to claim 1, which further comprises a pair of porous filters securely positioned in a spaced relation to one another within the channel where the bed of chromatographic separation material is positioned within the channel intermediate the pair of porous filters.

12. The column according to claim 11, wherein the filters comprises porous plastic.

13. The column according to claim 12, wherein the plastic is selected from the group consisting of polyvinylidene difluoride, cellulose, polysulfone, polypropylene, nylon and polytetrafluoroethylene.

14. The column according to claim 1, wherein the separation material comprises silica, cellulose, dextran, agarose, sepharose, sephadex, hydroxyapatite and paired-ion chromatography system resin.

15. The column according to claim 1, which further comprises a cap for sealing the channel proximal to the top end face by securing engaging the walls of the channel.

16. The column according to claim 15, wherein the cap comprises a closed male luer taper.

17. A kit for column chromatography comprising:
(a) A chromatography column according to claim 1;
(b) A cap for sealing the channel proximal to the top end face of the chromatography column for firmly engaging the walls of the channel of chromatography column;
(c) A collecting tube comprising a hollow body having a closed bottom end face and a top end face having an aperture therethrough for receiving the keying means of the chromatography column, said hollow polymer body having a generally circular shape along the length of the outer surface of the tube, and at least one keying means on the outer surface of the tube which interrupts the generally circular shape of the outer surface thereof, positioned between the two end faces of tube; and
(d) A rack having means for receiving the chromatography column and the collecting tube, said rack comprising a top surface having apertures therethrough, some of said apertures for receiving the keying means of the chromatography column and some of said apertures for receiving the keying means of the collecting tube, and a plurality of legs sufficient to support the surface of the rack.

18. The kit according to claim 17, which further comprises a pair of porous filters positioned in a spaced relation to one another within the channel of the chromatography column and a bed of chromatographic separation material positioned within the channel of the chromatography column intermediate the pair of porous filters.

19. The kit according to claim 18, wherein the chromatographic separation material is paired-ion chromatography system resin.

20. A column chromatography apparatus comprising:
(a) a column comprising:
(i) a body having an open top end face and an open bottom end face, and a channel having at least one porous filter positioned within the channel and having a bed of chromatographic separation material positioned within the channel adjacent the porous filter, said channel extending through the body from the top end face to the bottom end face, the diameter of the channel at the bottom end face being smaller than the diameter of the channel at the top end face, said channel being generally circular and tapered from the top end face to the bottom end face; (ii) means positioned at the top end face of the column for securely coupling the column to insertion apparatus having reciprocal coupling means; and (iii) at least one keying means on the outer surface of the column, which interrupts the generally circular shape of the outer surface thereof, positioned between the two end faces of the column for preventing rotation of the column when the keying means engages a complementary surface; and
(b) a collecting tube comprising:
(i) a hollow body having a closed bottom end face and a top end face having an aperture therethrough for receiving complementary keying means; and
(ii) at least one keying means on the outer surface of the tube, which interrupts the generally circular shape of the outer surface thereof, positioned between the two end faces of the tube.

21. The apparatus according to claim 20, wherein the outer surface of the tube defines a first segment having a generally circular shape in cross section and generally uniform in cross section along the length thereof, a second segment having a generally circular shape in cross section, and a third segment having a generally circular shape in cross section and tapered from one end of the third segment to the other end of the third segment.

22. The apparatus according to claim 21, wherein the keying means of the collecting tube comprises a generally flat, planar surface formed on the outer surface of the second segment of the tube.

23. The apparatus according to claim 20, wherein the body of the collecting tube comprises material selected from the group consisting of polymer and glass.

24. The apparatus according to claim 20, wherein the aperture of the collecting tube has a generally circular shape, interrupted by at least one flat, planar surface adapted to receive reciprocal generally cylindrical configurations.

25. The apparatus according to claim 20, wherein the top end face of the collecting tube is removable.

26. The apparatus according to claim 25, wherein the top end face of the collecting tube comprises a cap being adapted to securely fasten to the body of the tube opposite the bottom end face.

* * * * *